(12) United States Patent
Fromme et al.

(10) Patent No.: US 8,314,712 B2
(45) Date of Patent: Nov. 20, 2012

(54) BULK GRAIN STORAGE SPOILAGE DETECTION APPARATUS

(75) Inventors: Guy Fromme, Louisville, CO (US); Timothy O'Connor, Lafayette, CO (US)

(73) Assignee: Bin Tech L.L.L.P., Louisville, CO (US)

( * ) Notice: Subject to any disclaimer, the term of this patent is extended or adjusted under 35 U.S.C. 154(b) by 300 days.

(21) Appl. No.: 12/753,419

(22) Filed: Apr. 2, 2010

(65) Prior Publication Data

US 2011/0241889 A1  Oct. 6, 2011

(51) Int. Cl.
- G08B 17/10 (2006.01)
- G08B 23/00 (2006.01)
- G01N 1/00 (2006.01)

(52) U.S. Cl. ....... 340/632; 73/23.41; 340/633; 340/634; 340/693.6

(58) Field of Classification Search .......... 340/632, 340/602, 584, 581, 693.6; 73/23.41, 23.42
See application file for complete search history.

(56) References Cited

U.S. PATENT DOCUMENTS

| | | | |
|---|---|---|---|
| 5,155,019 A * | 10/1992 | Sussman et al. | 435/34 |
| 5,357,781 A | 10/1994 | Tikijian | |
| 5,791,236 A | 8/1998 | Schouten | |
| 6,711,470 B1 | 3/2004 | Hartenstein et al. | |
| 6,986,294 B2 * | 1/2006 | Fromme et al. | 73/865.8 |
| 7,208,187 B2 | 4/2007 | Gabler | |
| 7,219,532 B2 * | 5/2007 | Tipler et al. | 73/23.42 |
| 2009/0272836 A1 * | 11/2009 | Byrd et al. | 242/563 |

* cited by examiner

Primary Examiner — Benjamin C Lee
Assistant Examiner — Adnan S Shams
(74) Attorney, Agent, or Firm — Holland & Hart LLP

(57) ABSTRACT

An apparatus is disclosed for facilitating spoilage detection in bulk grain storage bins via dust-free or substantially dust-free air sampling. Dust particles are passively removed from sampled air without the use of barrier filters or electrostatic screens, but instead through the use of a non-linear pathway that is open at one end and closed at the other end. A system is disclosed that incorporates a coiled pathway as an air inlet element combined with a carbon dioxide or other gas detector element to provide an integrated detector module suitable for permanent installation in a dusty bulk grain storage bin environment to provide spoilage gas measurements over time. The system may communicate data to a central data storage system via cellular telephone or long range radio frequency data transmission. Alerts and alarms are generated and transmitted electronically to users via email, SMS text, automated phone messages and other means.

16 Claims, 12 Drawing Sheets

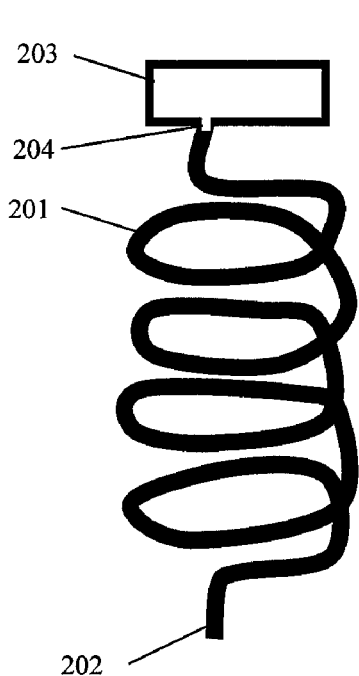
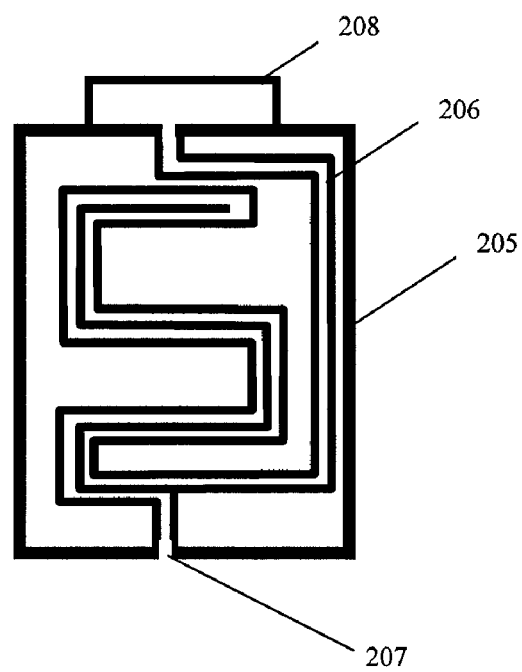
FIG. 2A
FIG. 2B
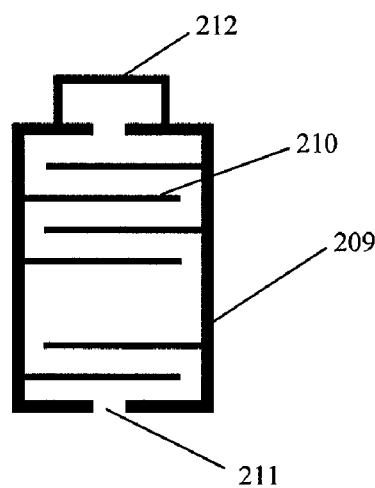
FIG. 2C

BULK GRAIN STORAGE SPOILAGE DETECTION APPARATUS

BACKGROUND

The world's grain processing industry has always experienced losses due to spoilage of harvested grain in long-term storage. Poorly controlled moisture and temperature conditions within a grain mass foster undesirable chemical and biological breakdown of grain kernels due to mold and insect growth, leading to a chain reaction of spoilage that often spreads widely within a storage bin. The adverse economic impact of spoilage is well known. In the United States alone, total annual storage losses are estimated at more than $1 billion. Worldwide, 10 to 20 percent of the global grain harvest is lost each year to improper or inefficient storage and handling. In the words of Patricia Woertz, CEO Archer Daniels Midland Company, "Clearly, agriculture must do better. Preserving what is already grown is critical . . . Mitigating post-harvest losses is part of a four-part approach needed to ensure agriculture's ability to fulfill the world's increasing food and energy needs." (address to World Economic Forum Annual Meeting, Davos, Switzerland, 1-27-2010).

This long-felt problem has spurred the development of technological solutions to augment or supplant human-based surveillance of grain stocks. The persistent need for a solution is evident in the proliferation of so-called temperature cable systems, which are in wide use for the purpose of monitoring stored grain temperature. A temperature cable's linear array of thermal sensors detects spoilage by detecting the heat generated by an exothermic chemical or biological spoilage event. This basic functionality has made temperature cables a well known product in the market. OPI Systems with their StorMax temperature cable product line, SafeGrain with their SafeTrack temperature monitoring system and Rolfes @Boone with their BCS 1000 temperature cable monitoring product are all companies that have benefited from the commercial success of this technology.

The elapsed time between the development of a quality problem in stored grain, detection of the problem and performance of necessary mitigation actions has always been critical to the economic viability of any grain storage, transshipment or processing operation. Non-automated labor intensive surveillance methods have traditionally been slow and unreliable, resulting in large losses due to undetected spoilage. The proliferation of temperature cable systems has led to more repeatable measurements, but it has essentially automated a relatively slow detection process. Because of the insulation properties of grain, the generation of detectable temperature changes in the grain mass may lag the growth of economically significant spoilage by days or weeks. This, in turn, has led many grain managers to continue a costly human-based quality surveillance regimen despite the presence of a temperature monitoring system.

Despite common use of temperature cable systems throughout the grain storage industry, undetected spoilage and huge losses from stored grain inventories is a common event. Even though they are considered to be an incremental improvement over exclusively human-based grain surveillance, temperature cables have a significant shortcoming. It is well known that the thermal impedance of the monitored grain inhibits the effectiveness of spoilage detection due to the need to be very close to the heat generating site. Because of the low thermal conductivity of bulk grain, a single temperature measurement must be within about 0.5 m (Sinha and Wallace, 1965) or less of an active spoilage spot to detect the self-heating. This thermal insulation, and associated proximity requirement, results in blind zones where temperature cables cannot sense grain condition. In order for a storage site operator to detect spoilage with 100% reliability, a prohibitively large number of cables would be required to ensure no portion of the bin volume was outside the thermal insulation distance.

Furthermore, because of the low thermal conductivity of grain, self-heating can lead to spontaneous combustion or smoldering which, if undetected, can result in a fire inside the grain bin, a direct threat to physical plant and personnel safety.

Grain spoilage has historically been the root cause of another unfortunate safety issue, grain engulfment accidents. Spoiled grain can cause a number of unsafe conditions inside a grain bin, including the formation of crusted grain bridges and large accumulations of grain adhered to the sidewalls of a bin. Very often, when workers enter grain bins with these conditions present, the surface crust or sidewall accumulations unexpectedly give way and workers become engulfed in an avalanche of grain. Such accidents often lead to injury or suffocation and continue to be a cause for concern among grain storage facility managers, farmers and government safety agencies such as OSHA.

SUMMARY

The present disclosure provides air sampling systems that avoid the above-described problems and meet the above-described needs. Embodiments disclosed herein take advantage of a phenomenon common to all spoilage modalities: the generation of excess carbon dioxide ($CO_2$) and its spread throughout the grain mass and into the grain bin headspace air. Sensitive $CO_2$ detectors disclosed herein can respond to the first telltale emissions from a nascent spoilage site to provide earlier warning than temperature cables with the convenience and cost-effectiveness of a singular or unitary hardware installation.

One aspect of this disclosure provides a sensor system that passively decreases air velocity to zero, or near-zero, along a diffusion path that allows entrained dust to fall out of the air before the diffusing molecular species of interest reaches a gas detector. In other words, the system allows the air sample to reach the detector substantially or completely dust-free without the use of a pre-filter. In one embodiment, a coiled tube closed at one end eliminates the need for filtering air when installed inside a grain bin. Because the dust-laden air must travel through a long tubular path, dust that falls out of the air is distributed along a large horizontal surface along the length of the tube. As a result, the tube cross section remains clear to air diffusion for very long periods of exposure, leading to maintenance intervals approaching the operating life of the sensor itself. The fact that air velocities within the tube reach substantially zero, and particles fall out of entrainment, greatly reduces the complexity and cost of air sampling subsystems for grain bin gas detectors of embodiments using such a tube. Other embodiments include dust-explosion-proofing through the addition of a thin membrane-type filter at the outlet end of the tube or channel. Such an optional barrier filter or membrane at the outlet end of the coil will only come into contact with gases from which substantially all dust particles have been eliminated via velocity reduction, and will rarely, if ever, be subject to clogging or fouling, therefore requiring little or no maintenance cleaning. Field trials of the coiled tube have proven that such a barrier membrane or filter is unnecessary. Forced gas or pressurized sampling systems are inferior to the present disclosed apparatus because they depend on actively moving a volume of gas through a barrier filter or membrane, leading to dust buildup and degraded gas flow. Furthermore, since no power is needed to bring air samples to the sensor of the disclosed sensor system, the use of such a long-life passive dust removal device enables low power and remote battery-powered gas analysis systems for grain bins.

The dust exclusion coil of various embodiments described herein incorporates a coil of tubing of any suitable material with an inside diameter of at least 0.125 inch. The coil is at least one full turn with the minimum allowable turn radius governed by the coil material. The coil may be contained within a housing that is open at the "down end" and closed at the "sensor end" with a through hole for attachment of the outlet end of the coil. If the gas detector is installed in a location with high ambient air currents or vortices, then the number of coil turns or channel reversals can simply be increased to lengthen the settling path along which dust may settle out of the sampled air.

More specifically, in one aspect the present disclosure provides an apparatus for facilitating spoilage detection in bulk grain storage bins. Embodiments of this aspect operate by passively removing dust particles from sampled air without the use of barrier filters or electrostatic screens, but instead through the use of a non-linear pathway that is open at one end and closed at the other end. Such a non-linear pathway may be, for example, a coiled, serpentine, indirect, meandering, or circuitous path. By providing a diffusion path for gases without allowing a bulk gas transport path, substantially all entrained dust particles fall out of the air due to gravity without being transported to the gas detector while spoilage gas molecules reach the detector via diffusion. Any air currents near the vicinity of the inlet are rapidly dissipated inside the pathway due to direct impingement against the interior surfaces, leading to the shedding of excess kinetic energy. The result of this is that sample air at the other end of the pathway is substantially, if not completely, free of dust. The system of this aspect incorporates the non-linear pathway as an air inlet element combined with a $CO_2$ gas detector element to provide an integrated gas detector module suitable for permanent installation in a dusty bulk grain storage bin environment to provide $CO_2$ measurements over time. This system can be installed inside the grain bin under the roof, in the plenum of a grain bin aeration system, or directly in the path of such a system's air exhaust stream. In some embodiments, the system communicates data to a central data storage system. Such communications may be accomplished through wired or wireless data connections, such as via cellular telephone or long range radio frequency data transmission. Another embodiment provides a system that uses integrated temperature and relative humidity sensors as part of a weather station that records conditions inside and outside the grain bin over time. Another embodiment provides a system that assesses undesirable trends and patterns in the $CO_2$ data and provides appropriate grain condition alerts or alarms to the user. Still further aspects of the present disclosure provide systems comprised of multiple $CO_2$ sensor systems in communication with each other. Communication may be accomplished through wired or wireless communications, such as via short range radio frequency data transmission and reception. Such a collection of $CO_2$ sensor systems comprises a network and communication from and to the network may be accomplished via cellular telephone or long range radio frequency data transmission. In one embodiment, the network transmits data to a central data storage system where trends and conditions are assessed in each monitored grain bin. Alerts and alarms are generated and transmitted electronically to users, such as via email, SMS text, automated phone messages and other means.

In the past, a grain manager's effectiveness was limited by the physical arrangement of the assets he managed as well as the number of personnel available for grain surveillance at any particular time. Realization of economies of scale in grain handling and storage has seen the average acreage per farm and the number of storage tanks under common management radically increase. Hundreds of tanks at a single site or thousands spread across tens or hundreds of miles are much more difficult to manage than historically smaller numbers at single sites. The present invention enables a grain manager to monitor stored grain in any number of grain bins at any number of sites at any locations via simple internet web-based access. This network or mesh replaces costly visits by personnel that are fuel-, labor- and time-intensive and increases detection effectiveness well above temperature-based or human nose-based methods.

A network is created whenever two or more $CO_2$ detector systems are installed to collect $CO_2$ data from the associated grain bins. One detector system acts as the local master node and all other detector systems at the site transmit their data to the local master node via short range radio frequency communication. All of the site $CO_2$ data are aggregated by the local master node and periodically transmitted to the central data storage system via cellular telephone data communication. Configuration commands and status inquiries are sent to a site local master node, in receive mode, via cellular telephone data communication and are distributed to individual $CO_2$ detector systems, also in receive mode, from the local master node, in transmit mode, via short range radio frequency communication. This arrangement and interaction architecture is also known as the local communication and control mesh. The alert/alarm processing software runs in conjunction with the central data storage system, tracking $CO_2$ concentration trends in each monitored storage tank. When the trend parameters in a given tank satisfy one or more criteria, including but not limited to high value, persistence, peaking or peaking frequency, an alert or alarm condition is set and a follow-up action is initiated to notify the user or grain manager.

Because $CO_2$ travels through a grain mass 30-40 times faster than heat, $CO_2$ level is a much more sensitive indicator of grain quality than temperature because spoilage will generate detectable excesses of $CO_2$ days or weeks before the same spoilage generates a detectable temperature increase. Using a $CO_2$ sensor provides the grain manager with a powerful double advantage—a simpler, single point monitoring system and one that provides an earlier warning of emergent quality problems. Academic research performed in cooperation with the inventors has proven the efficacy of this new method for detecting spoilage. Among the research publications directly related to this invention is D. E. Maier, et al., Monitoring Carbon Dioxide Concentration For Early Detection Of Spoilage In Stored Grain, 2009. $CO_2$ detection methods promise to shrink the time traditionally tolerated between spoilage and detection from months down to weeks and in some cases from months down to days.

Using one or more aspects of the present disclosure may provide grain storage facility managers and farmers with one or more new tools for reducing personnel safety hazards associated with entry into the confined spaces of grain bins. Rather than being forced to accept the development of severe spoilage conditions in poorly monitored grain bins as a cost of doing business, operators can use $CO_2$ detection, or other gas detection, to identify spoilage early in its growth cycle. Early spoilage identification allows the employment of less intrusive mitigation methods such as aeration, coring and top layer removal; these methods do not require entry by humans into affected bins, thereby increasing overall workforce safety.

BRIEF DESCRIPTION OF THE DRAWINGS

The present disclosure may be understood by reference to the following detailed description taken in conjunction with the drawings briefly described below.

FIGS. 2A-2C are diagrammatic illustrations of three embodiments of the dust exclusion pathway, a coiled tube, a serpentine channel embedded within a monolithic machined or injection-molded component, and a housing with internal baffles.

DETAILED DESCRIPTION

Figure 1:
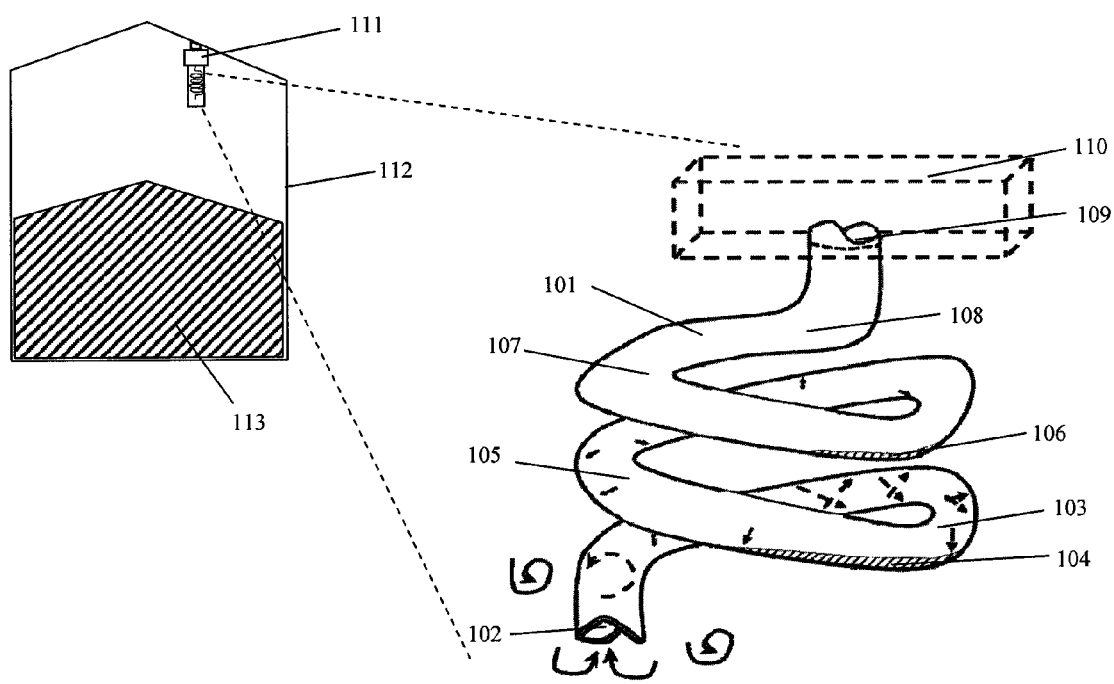
FIG. 1 is a diagrammatic illustration of a dust exclusion apparatus located in a grain bin comprised of a coiled or serpentine pathway with an inlet exposed to dust-laden air and an outlet emptying into an enclosed sampling space employed to passively exclude dust particles from the sampled air in accordance with one embodiment of the present disclosure.

The present disclosure recognizes that in dust-laden grain bin environments, air sampling is complicated by the necessity to remove airborne particulates from sampled air to avoid problems associated with particulate build-up on or clogging of sensor components. Particulate build-up, or fouling, decreases measurement sensitivity or may completely block the air path to the sensor, skew sensor calibration, reduce sensor life, decrease the maintenance interval and ultimately increase the overall cost of ownership.

Filtering schemes may be used to separate entrained particles from sample air by the use of barrier membranes or electrostatic grids with porosity appropriate for the size of particles that must be blocked. Barrier filtering, however, is often inappropriate for permanently installed gas detectors due to fouling and blocking. The use of filters may reduce the problems associated with particulate fouling, but does not eliminate the cost and downtime related to filter maintenance. In dusty applications, an active sampling system is often chosen to increase sample volumes, make successive sample volumes equal for successive calibrations, increase measurement sensitivity and decrease the impact of filter clogging by forcing air through the system. While active samplers can operate longer between filter maintenance intervals, passive sampler filters quickly clog to levels that impair sensor performance. The filter problem would effectively cancel the low cost advantage inherent in passive air sampling systems for gas detectors installed in the dust entrained environment of grain bins.

Gabler (U.S. Pat. No. 7,208,187), Hartenstein, et al (U.S. Pat. No. 6,711,470) and Schouten (U.S. Pat. No. 5,791,236) all teach the use of $CO_2$ sensing in air for the purpose of knowing or controlling the atmosphere composition for fruits and vegetables in storage or transit to minimize spoilage; Tijikian (U.S. Pat. No. 5,357,781) teaches gas sampling and detection from fluids; however, none of these methods extends to the application of sensing $CO_2$ in air within a dusty grain storage bin or ground storage pile. Fromme, et al (U.S. Pat. No. 6,986,294) teaches the incorporation of a gas sensor as part of a grain storage monitoring system, but does not enable a passive dust exclusion and air sampling method.

Most grain is stored for some period of time following harvest prior to transshipment and end use. This storage time has always been a risk to grain quality and, thus, to profit margins for grain producers and merchandisers. Any time spent by grain under static storage conditions holds the potential for the progression of spoilage. This is a worldwide problem with typical annual losses of 10%-30% and more due to late detection and runaway spoilage. Ideal storage conditions can often seem contradictory to grain managers, for example, the inverse relationship of moisture content and optimal storage temperature. The complexity often leads to confusion and thus a need for expert environmental measurement and advising systems. In the past, grain managers, both in commercial and on-farm settings, relied on labor-intensive storage container surveillance consisting of periodic visits to each storage tank to maintain current knowledge of the stored grain's quality. Each visit entailed opening the tank hatch and smelling the headspace air to detect any telltale off odors that might indicate a developing quality problem. In addition, a technique known as "walking the grain" was typically used to determine if the grain pile's surface had developed a crust, also indicative of a quality problem. These techniques relied heavily on the experience of the person making the surveillance visits and there were problems with consistency and repeatability from one person to another.

The labor cost and unreliability associated with human-based grain surveillance led to the development and proliferation of automated quality monitoring systems based on temperature measurements in the grain mass. Spoilage and to a lesser degree, insect activity, generate excess heat, raising the temperature of the local grain mass within about a meter of the problem site. An array of temperature sensors located throughout the grain mass can detect these hot spots as long as they are within the insulating distance characteristic of the grain being monitored, normally less than 1 meter, and the spoilage location is hot enough to register a temperature difference compared to adjacent thermal sensor readings. Unfortunately, the cost of installing temperature sensors at <1 m intervals throughout the grain pile in even moderate size grain bins is prohibitively high. Grain managers interested in automating their quality surveillance operations have always been forced to compromise on coverage versus cost, installing cables at 2, 3 and 5 meter intervals, and leaving large volumes of the stored grain unmonitored. The result is that a spoilage problem must grow to an undesirably large size for the heat generated to influence the nearest temperature sensor.

Several terms are used repeatedly throughout this disclosure and the following definitions provide a description of the meaning of several of these terms.

Grain—any dry, bulk agricultural seed or seed by-product including, but not limited to, wheat, barley, millet, corn, sorghum, soybeans and oats or partially processed dry seeds, for instance, cracked wheat and rolled oats; the term grain can also denote mixtures of such seeds or seed by-products.

Spoilage—biological growth condition in stored grain responsible for loss of quality and caused by uncontrolled factors including, but not limited to, bacteria, mold and insect infestation, made worse by excessive moisture and/or temperature.

Grain bin—generic term for structures used to store grain in bulk form, such as steel bins, concrete silos, flat storage buildings, horizontal silos; particularly structures with >500 bushels of storage capacity. Grain is also often stored in temporary or permanent ground piles.

Headspace—the airspace within a grain bin located between the roof or ceiling and the top surface of a mass of stored grain.

Tube—enclosed channel or duct of appropriate length with generally circular cross section, although other cross sections may be used, such as oval, square or rectangular cross sections.

$CO_2$—carbon dioxide in gaseous state.

FIG. 1 depicts an embodiment of an apparatus for passively excluding dust, present in grain bin headspace, from a gas sensing system 111 permanently installed inside a grain bin 112 for the purpose of monitoring stored grain 113 for spoilage. Since no power is needed to bring air samples to the sensor, the use of a long-life, passive, filterless dust removal device enables low power and remote battery-powered, permanently installed gas detection systems for grain bins. This is accomplished by using a coiled tube 101 composed of a suitable material or materials with an inlet end 102, an outlet end 109 and an open gas flow path from end to end to allow molecular diffusion to occur from inlet to outlet. Bulk air transport through the coil is prevented by a sealed box enclosure 110 at the outlet end where a gas detector is typically located. By providing a diffusion path for sample gases without allowing a bulk gas transport path, substantially all entrained dust particles fall out of the air due to gravity without being transported to the gas detector. Any air currents near the vicinity of the inlet 102 are rapidly dissipated inside the tube 101 or channel due to direct impingement against the interior surfaces, leading to the shedding of excess kinetic energy. Eddy current velocity inside the tube 101 is reduced by direct impingement of dust-laden air against the tube's inner walls 103 resulting in some settling out of entrained dust 104. Further along the interior of the tube 101, the eddy current velocities are progressively reduced 105 due to additional impingement against the tube walls 103, resulting in more dust fallout 106 until the eddy current velocities are reduced substantially to zero 107 and the sample air at the other end of the tube or channel is substantially free of dust 108. In other words, the turns of the coil or twists of the channel serve to reduce the velocity of dust-laden air from speeds common to headspace air currents in grain bins down to zero or nearly zero speed by direct impingement against the interior walls of the tube or channel. This shedding of kinetic energy allows entrained particles to fall out of the air via gravity inside the tube before reaching the outlet end. The axis of the coil can be oriented in any direction and the inlet and outlet ends can be located in any position relative to each other and the coil body. Multiple parallel coils and multiple interconnected coils are also alternate embodiments of the configuration illustrated in FIG. 1, a single coil with one inlet and one outlet.

FIG. 2A illustrates that the coiled tube configuration can be constructed as a simple helical arrangement of a single tube 201 with an open inlet 202 where dust-laden air enters and a closed outlet 203. The action of the coiled pathway yields substantially dust-free air at the outlet 204. FIG. 2B shows another embodiment in which the serpentine pathway is enclosed within a mass of material 205, the pathway either drilled out or formed as a result of mating sections of machined or injection molded material 206, with an inlet 207 and a closed outlet 208. FIG. 2C shows an additional embodiment in which the serpentine pathway is implemented through the use of a series of baffles installed within a housing or enclosure 209, the pathway formed as a result of alternating baffles or separators 210, with an inlet 211 and a closed outlet 212. Of course, one of skill in the art will readily recognize numerous other alternatives for providing a pathway that reduces air velocities that may be present at an inlet to substantially zero and thereby provide sample air at the other end that is substantially free of dust.

Figure 3:
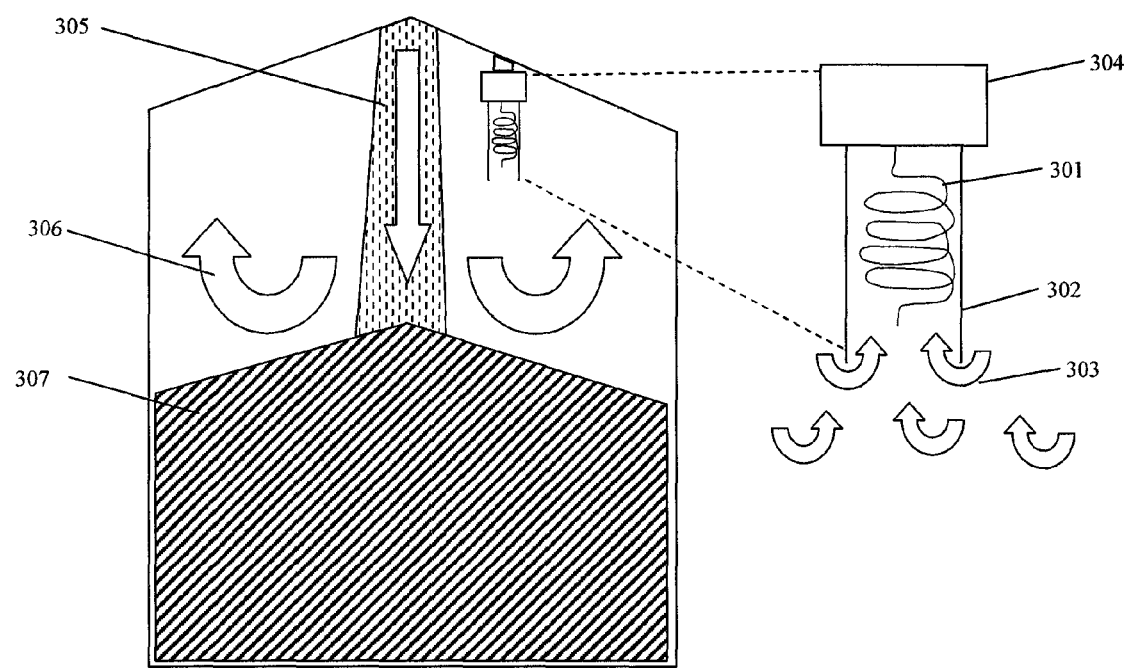
FIG. 3 is a diagrammatic illustration of an embodiment including a coiled pathway passive dust exclusion device as part of a permanently installed detector instrument within a bulk grain storage bin, also showing the dust generating properties of the grain loading process.

FIG. 3 depicts a permanently installed gas detector assembly incorporating the passive, filterless dust removal device, in this case a coil of tubing 301, within a cylindrical shroud 302 that helps to further reduce incident air velocities entering from the surrounding headspace air 303 and with the outlet of the coil emptying into a detector enclosure 304. Severe dust conditions are common for permanently installed equipment due to, for example, dumping of grain 305 through the roof of the grain bin. This entering grain creates large amounts of dust that becomes entrained in the headspace air 306 over the surface of the stored grain 307.

Figure 4:
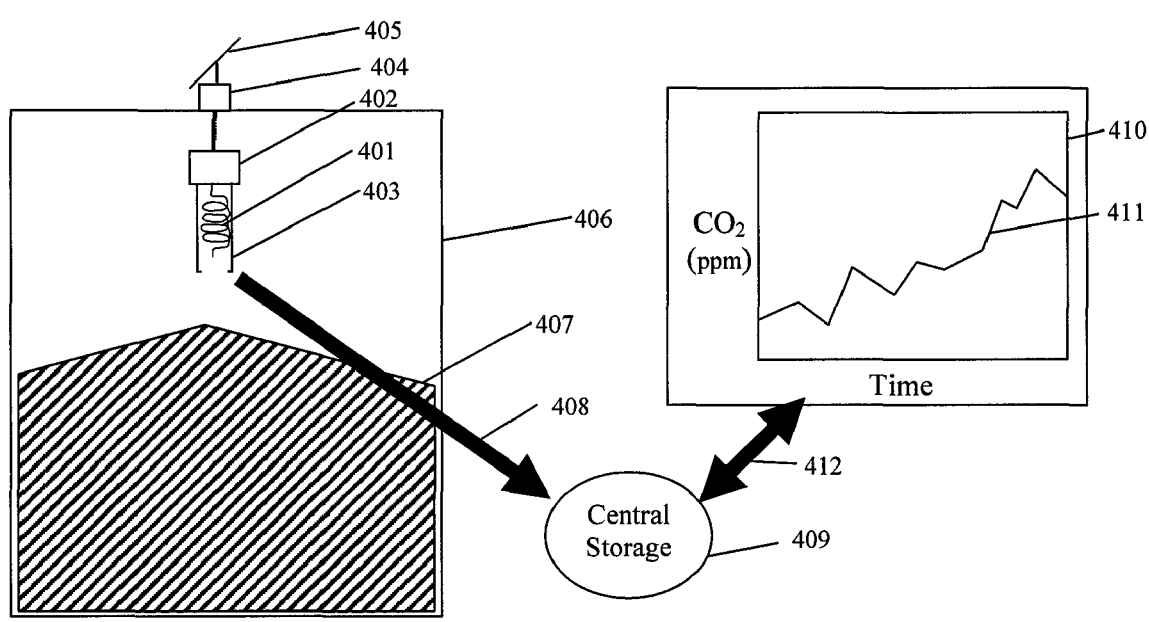
FIG. 4 is a diagrammatic illustration of a system incorporating the dust exclusion pathway, a $CO_2$ detector, solar panel and battery, and a means of transmitting and displaying the $CO_2$ concentration as measured over time in accordance with an embodiment of the present disclosure.

FIG. 4 depicts a $CO_2$ detection system that incorporates the passive, filterless dust removal device, represented as a coil 401, the $CO_2$ detector enclosure 402, a cylindrical shroud to reduce ambient air velocities 403, a battery and charging control electronics 404, and a solar photovoltaic panel for generating battery recharging current 405. Power for the $CO_2$ detector system can be provided by traditional cabled power transmission or by a battery and an integral photovoltaic solar collection panel for battery recharging. The system detects grain spoilage in grain bins 406 by determining the absolute $CO_2$ concentration in the headspace over any mass or collection of stored grain 407 inside a grain bin. Spoilage generates detectable excesses of $CO_2$ days or weeks earlier than alternative temperature-based technology, making $CO_2$ detection more capable than temperature detection. This provides the grain manager with a simpler monitoring system that provides an earlier warning of emergent quality problems. This spoilage detection system incorporates the previously disclosed coiled pathway passive dust exclusion device. The $CO_2$ detector system identifies $CO_2$ molecules by monitoring the molecular light emission properties of gas in a sampling chamber. $CO_2$ developed in a grain mass is transported by aeration, convection and molecular diffusion throughout the adjoining free air mass, including the measurement chamber of the $CO_2$ detector. $CO_2$ concentration is measured and reported in parts per million (ppm). Elevated $CO_2$ concentrations are often indicative of increased spoilage in the monitored mass of grain. The system, using an on-board processor, periodically measures the $CO_2$ concentration and stores each measurement in a data list or file to create a history of $CO_2$ concentration through time. Temperature and relative humidity measurement capability can be added to this system.

These data are periodically transmitted or uploaded to a central data storage system 409. The transmission of data to the central data storage system 409 may be accomplished using any suitable communications medium, and in the embodiment of FIG. 4 is accomplished via a cellular telephone or long range radio frequency data link 408 to a central data storage system 409. Data for the stored grain may be displayed on graphical charts 410 depicting the $CO_2$ concentration data over time 411, which may be made available for inspection by operators or managers via, for example, an internet computer connection 412 to the central data storage system. A cellular data modem and a radio frequency transmitter/receiver provide wide area and local area data communication, respectively, in this embodiment.

Figure 5:
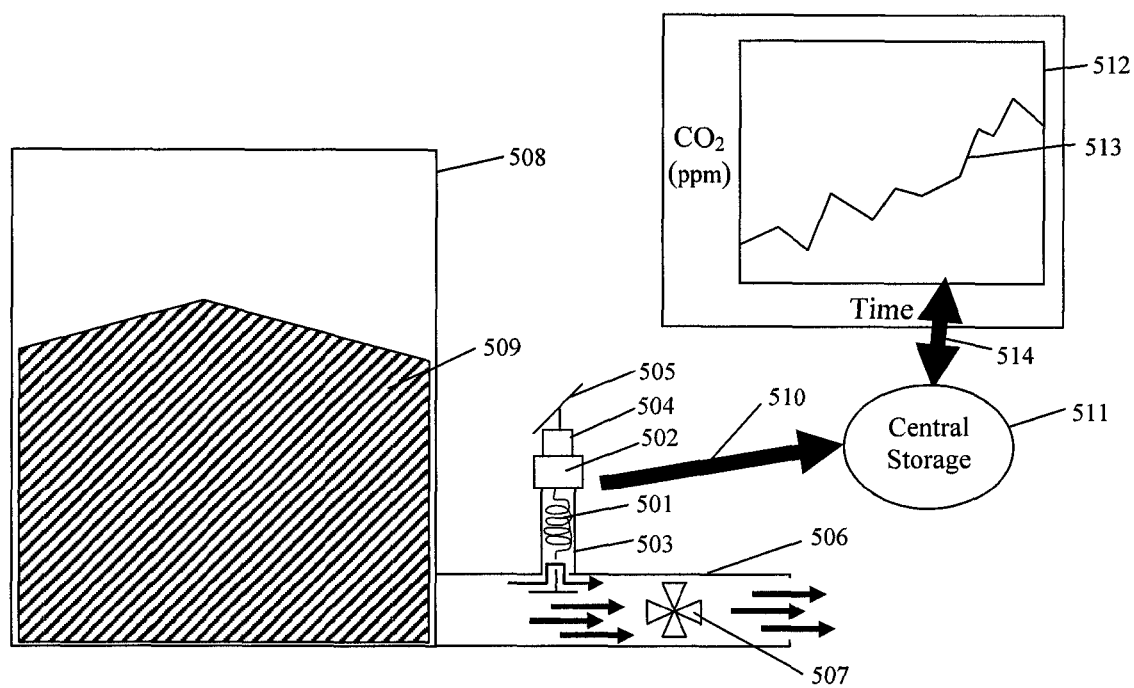
FIG. 5 is a diagrammatic illustration of a system installed at an aeration plenum incorporating the dust exclusion pathway, a $CO_2$ detector, solar panel and battery, and a means of transmitting and displaying the $CO_2$ concentration as measured over time in accordance with an embodiment of the present disclosure.

FIG. 5 illustrates an embodiment that incorporates the passive, filterless dust removal device, represented as a coil 501, the detector enclosure 502, a cylindrical shroud 503 to protect against weather, a battery and charging control electronics 504, and a solar photovoltaic panel for generating battery recharging current 505, all mounted at an aeration plenum or duct 506 in close proximity to the aeration fan 507 and exhaust air stream. This embodiment can be applied to grain bins as well as to temporary and permanent ground storage piles. Alternatively, for push-style aeration systems, the airflow is directed into the stored grain mass by the fan, then up and out of the grain bin through roof vents where a $CO_2$ detector system would be installed. Power for the $CO_2$ detector system can be provided by traditional cabled power transmission or by a battery and an integral photovoltaic solar collection panel for battery recharging. The system detects grain spoilage in grain bins 508 by determining the absolute $CO_2$ concentration in the headspace over any mass or collection of stored grain 509 inside a grain bin. The $CO_2$ data are periodically transmitted or uploaded via, in this embodiment, a cellular telephone or long range radio frequency data link 510 to a central data storage system 511. Data for the stored grain may be displayed on graphical charts 512 depicting the $CO_2$ concentration data over time 513, which may be provided for inspection by operators or managers such as via an internet computer connection 514 to the central data storage system as illustrated in this embodiment.

Figure 6:
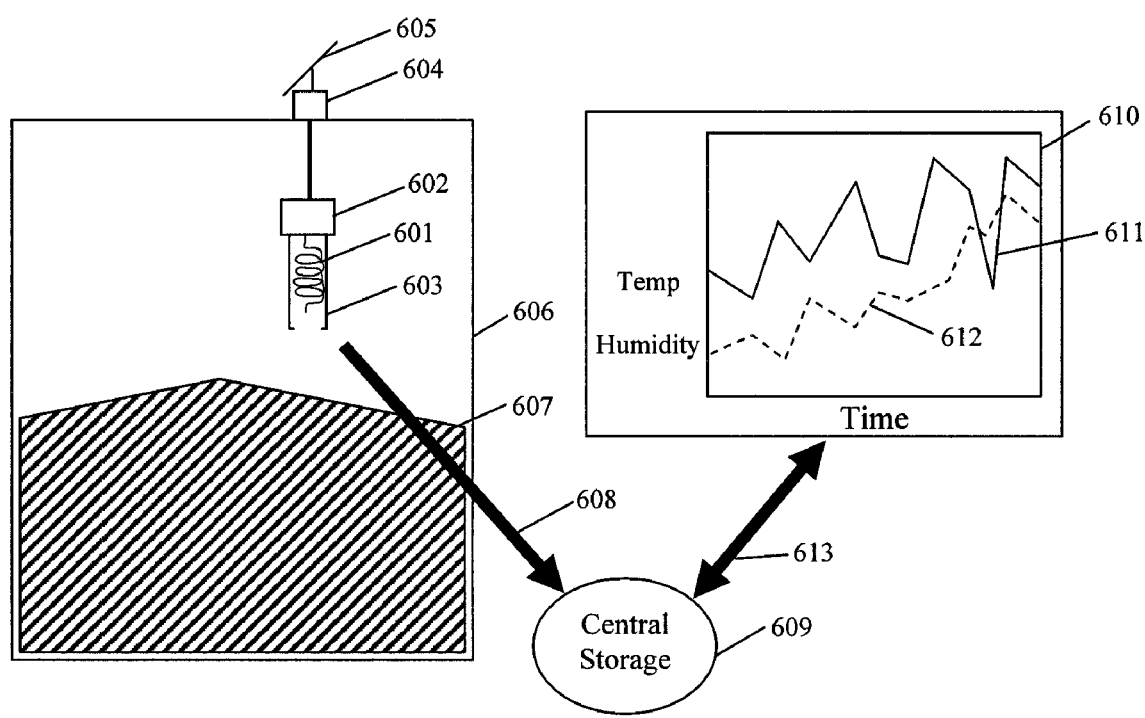
FIG. 6 is a diagrammatic illustration of an embodiment including an internal weather station incorporating a coiled pathway passive dust exclusion device as part of a permanently installed detector instrument within a bulk grain storage bin that measure temperature and relative humidity in the grain bin headspace.

FIG. 6 depicts another exemplary system for monitoring environmental conditions inside a grain storage bin. This in-the-bin weather station system incorporates the passive, filterless dust removal device, represented as a coil 601, an enclosure 602 for temperature and relative humidity detectors, a cylindrical shroud to reduce ambient air velocities 603, a battery and charging control electronics 604, and a solar photovoltaic panel for generating battery recharging current 605. Power for the in-the-bin weather station system can be provided by traditional cabled power transmission or by a battery and an integral photovoltaic solar collection panel for battery recharging. The system detects temperature and relative humidity in grain bins 606 by sensing the temperature and water concentration in the headspace air over any mass or collection of stored grain 607 inside a grain bin. These data are periodically transmitted or uploaded via, in this embodiment, a cellular telephone or long range radio frequency data link 608 to a central data storage system 609. The data for the stored grain may be displayed on graphical charts 610 depicting the temperature 611 and relative humidity 612 data over time, and made available for inspection by operators or managers via, in this embodiment, an interne computer connection 613 to the central data storage system. This data enables operators and managers to analyze data for safe, effective aeration decisions, provide dew point alerting and alarming related to condensing or dripping conditions and provide an additional indicator for spoilage risk. A cellular data modem and a radio frequency transmitter/receiver of this embodiment can provide wide area and local area data communication, respectively.

Figure 7:
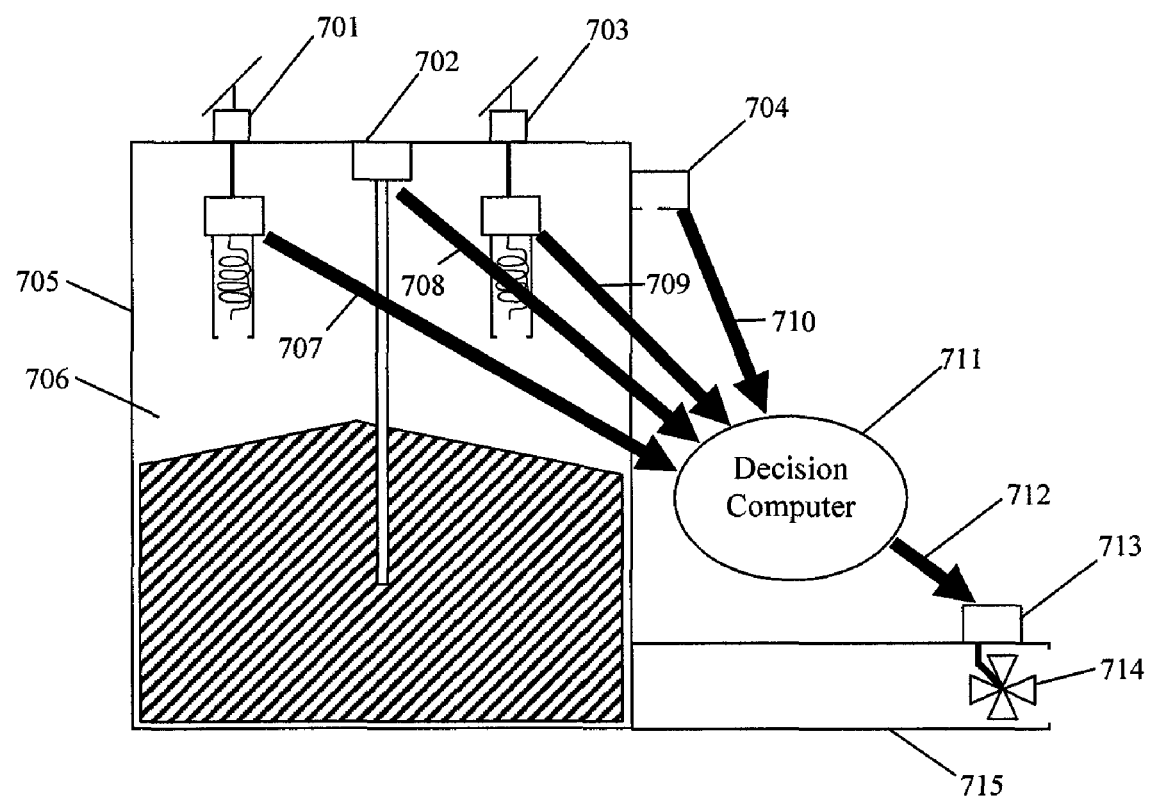
FIG. 7 is a diagrammatic illustration of an embodiment comprising several systems, including a $CO_2$ detector, a temperature cable, an internal weather station and an external weather station system, that provide spoilage and environmental condition data that are all used to control an aeration system to maintain quality of the stored bulk grain.

FIG. 7 shows another exemplary system for gathering data to provide automated aeration decision-making and automated aeration control for a grain storage bin. This system incorporates a number of permanently installed environmental and gas detectors which may include, but is not limited to, a $CO_2$ detector 701, a cable-based temperature and relative humidity detector 702, a headspace temperature and relative humidity detector 703, and an external temperature and relative humidity detector. The system collects available $CO_2$, temperature and relative humidity data from in and around a grain bin 705 and from the mass of stored grain within it 706. These data are transmitted via short range radio frequency or via hardwired cable connections, 707, 708, 709 and 710, to a decision subsystem or computer 711 for processing. The decision subsystem can be enabled to provide information regarding advancing cool fronts and moisture fronts within the grain mass and provide expert recommendations for aeration strategy relative to safe, effective aeration, dew point alerting and alarming related to condensing or dripping conditions and general spoilage risk, or can be configured to issue aeration control orders 712 to an aeration control unit 713 to operate an aeration fan 714. The fan pulls air through the grain mass and out through a duct or plenum 715.

Figure 8:
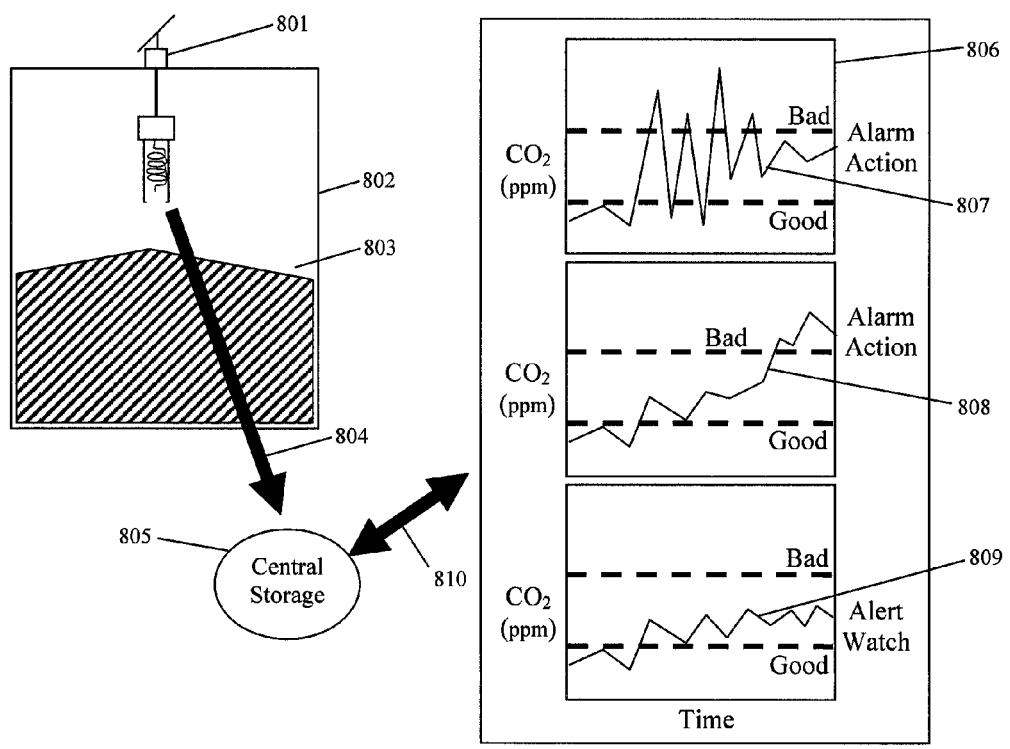
FIG. 8 is a diagrammatic illustration of a single grain spoilage detector system of an embodiment that provides for communicating $CO_2$ data from a monitored grain storage bin to a central data storage node where the data are processed for the presence of alert or alarm conditions and appropriate user messages are generated and transmitted.

FIG. 8 depicts an exemplary system for assessing $CO_2$ history information and making recommendations for actions related to the detected stored grain condition and quality. The system of this embodiment is comprised of the previously described $CO_2$ detector 801 which is permanently installed inside a grain bin 802 to monitor the stored grain mass 803. The $CO_2$ data is transmitted 804 to a central data storage and processing computer 805 via, in this embodiment, radio frequency techniques, long or short range as required. The system processes the $CO_2$ concentration history data and presents it for display as charts or tables 806. The system recognizes peaking 807 and slope trends 808 in the data to identify needs for alarm messaging to operators and managers of the monitored stored grain so that appropriate preventive and remedial actions can be taken. The system also recognizes data trends where absolute $CO_2$ levels are acceptable but merit an alert message 809 to operators and managers as a grain bin to watch without taking further action. The $CO_2$ data and alert/alarm status are available for inspection by operators or managers via, for example, an interne computer connection 810 to the central data storage system. The present invention shrinks the time traditionally tolerated between spoilage, detection and alerting from months down to weeks and in some cases from months down to days. $CO_2$ levels above those associated with normal ambient ranges or normal grain kernel respiration are used as baselines to assess the degradation of the condition or quality of the stored grain and, in particular, are used to create a grain quality history for the grain mass under surveillance. Adverse trends in the $CO_2$ concentration are monitored by a human operator or by a programmed computer system to identify problems related to spoilage. The system uses this information to notify the storage manager that mitigating actions are required as a result of degrading grain condition and/or quality. Assessment of mycotoxin risk based on grain bin data can also be provided by the computer system. The system performs notification via electronic means including, but not limited to email, SMS text messages and automated cellular telephone calls.

Figure 9:
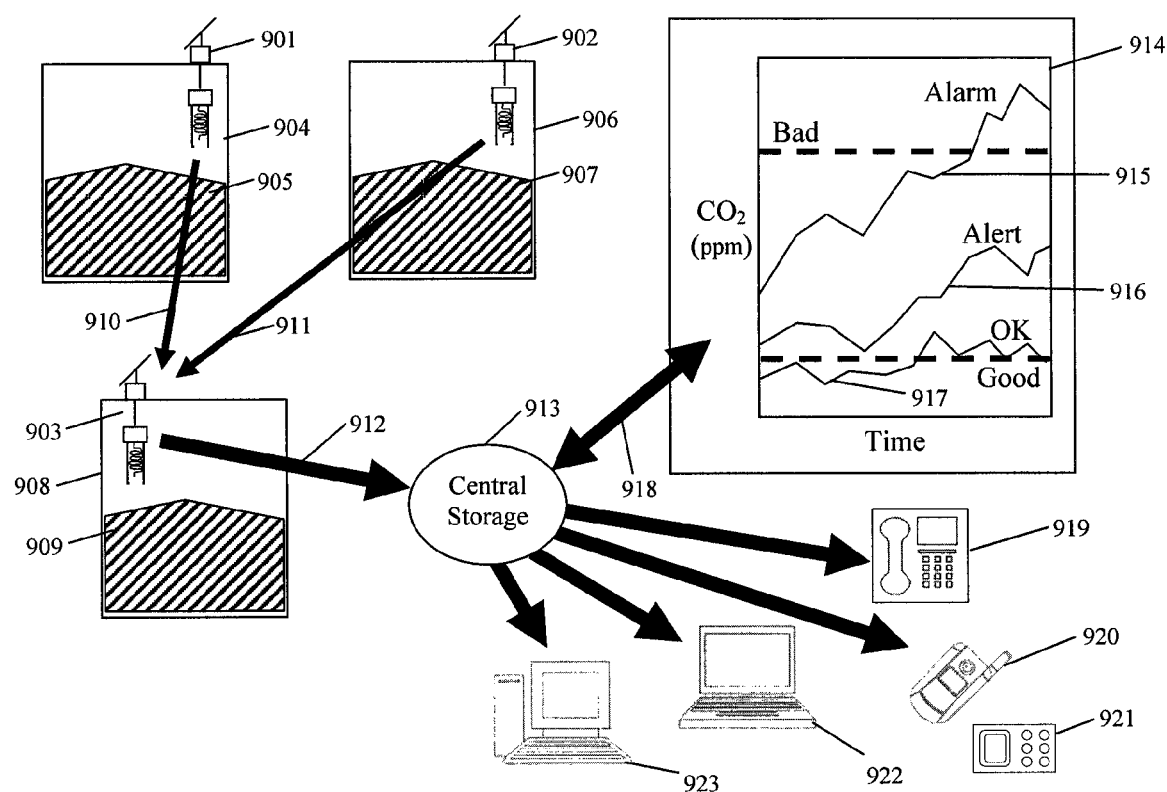
FIG. 9 is a diagrammatic illustration of an exemplary network of grain spoilage detector systems communicating $CO_2$ data from monitored grain storage bins to a central data storage node where the data are processed for the presence of alert or alarm conditions and appropriate user messages are generated and transmitted.

FIG. 9 illustrates a system that implements a network of $CO_2$ detectors to accomplish monitoring of stored grain in multiple grain bins at a single location, for an exemplary embodiment. The system of this embodiment is comprised of at least two previously described $CO_2$ detectors, in this case there are three 901, 902 and 903, permanently installed in grain bins 904, 906 and 908, monitoring different stored grain masses 905, 907 and 909. One of the $CO_2$ detectors 903 acts as a data collection and transmission node for this network of detectors. The other detectors send their data via short range radio frequency techniques, 910 and 911, to the collection node detector which, in turn, forwards all of the $CO_2$ data for the network of detectors 912 to a central data storage system 913 via long range radio frequency or cellular telephone techniques. Short range radio frequency data communication may be accomplished using one, or more, of a number of available techniques, such as through Bluetooth or Zigbee type networks, for example. The data is processed by the central data storage system and formatted for display 914 of $CO_2$ data over time for each monitored grain bin in the network, 915, 916 and 917, with appropriate alarms and alerts noted. The $CO_2$ data and alert/alarm status are available for inspection by operators or managers via, for example, an internet computer connection 918 to the central data storage system. In addition to handling information requests by internet connection, the central data storage system of this embodiment pushes alert and alarm messages to users and subscribers via hardwired telephone 919, wireless cellphone 920 and other handheld devices 921, mobile computers 922 and other computers 923. Any number of permanently installed detectors including, but not limited to, $CO_2$, air temperature, relative humidity and grain temperature, can be embedded in the same local communication network or mesh and communicate their data to the detector acting as the collection node via short range radio frequency techniques with the aggregated data forwarded by this collection node to a central data storage system via long range radio frequency or cellular telephone methods. Data communication among detectors in this mesh or network can also be performed over wires or via any combination of wired and wireless data links.

Figure 10:
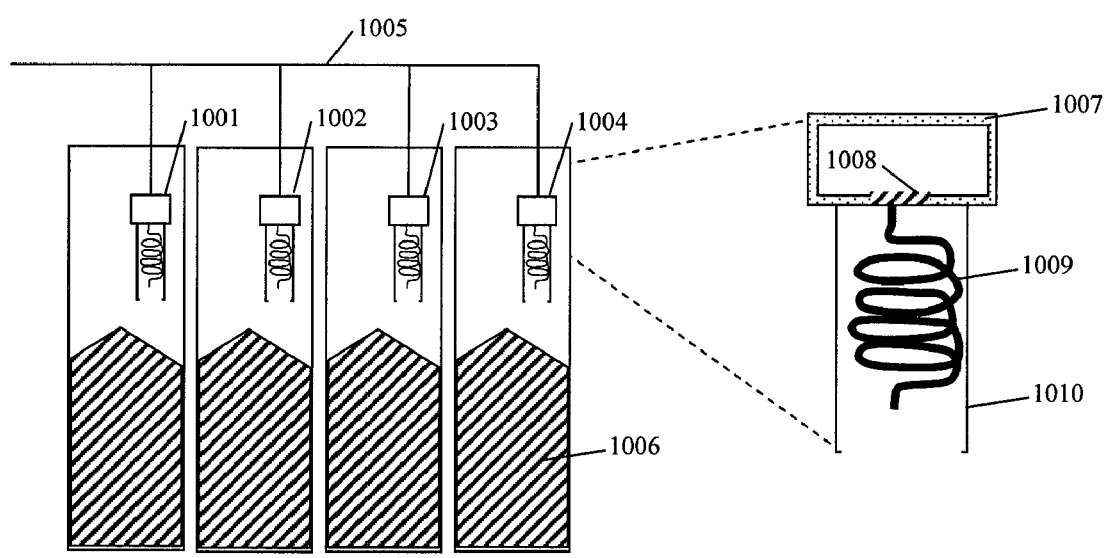
FIG. 10 is a diagrammatic illustration of a system of an embodiment incorporating a dust-explosion-proof enclosure, a barrier filter to interrupt spark paths and hard-wiring of power connections.

FIG. 10 depicts an exemplary system suited to commercial grain elevators and food processors where dust conditions demand specially designed equipment to meet the safety requirements of the application, particularly dust-explosion-proof equipment. The system is comprised of any number of $CO_2$ detectors, in this case four are shown 1001, 1002, 1003 and 1004, interconnected with power and data wiring 1005. These detectors are permanently installed in multiple grain bins 1006. Short and long range radio frequency and cellular connections can be employed as well as the solar photovoltaic and battery system for power. The $CO_2$ detectors incorporate dust-explosion-proof features including a thicker electronics enclosure 1007 and a dust path barrier filter 1008. Intrinsically safe electronic components and design rules may be included in the electronics enclosure. The detectors also include the filterless passive dust excluding device 1009, shown here as a coil, and a cylindrical shroud 1010 for further reduction of air velocities. As previously described, one of the $CO_2$ detectors acts as a data collection and transmission node for this network of detectors. The other detectors send their data via short range radio frequency techniques or over wires to the collection node detector which, in turn, forwards all of the $CO_2$ data for the network of detectors to a central data storage system via long range radio frequency or cellular telephone techniques. The data is processed by the central data storage system and formatted for display of $CO_2$ data over time for each monitored grain bin in the network with appropriate alarms and alerts noted. The $CO_2$ data and alert/alarm status are available for inspection by operators or managers via, for example, an internet computer connection to the central data storage system. Any number of permanently installed detectors including, but not limited to, $CO_2$, temperature and relative humidity, can be embedded in the same local communication network or mesh and communicate their data to the detector acting as the collection node via short range radio frequency techniques with the aggregated data forwarded by this collection node to a central data storage system via long range radio frequency or cellular telephone methods. Data communication among detectors in this mesh or network can also be performed over wires or via any combination of wired and wireless data links.

Figure 11:
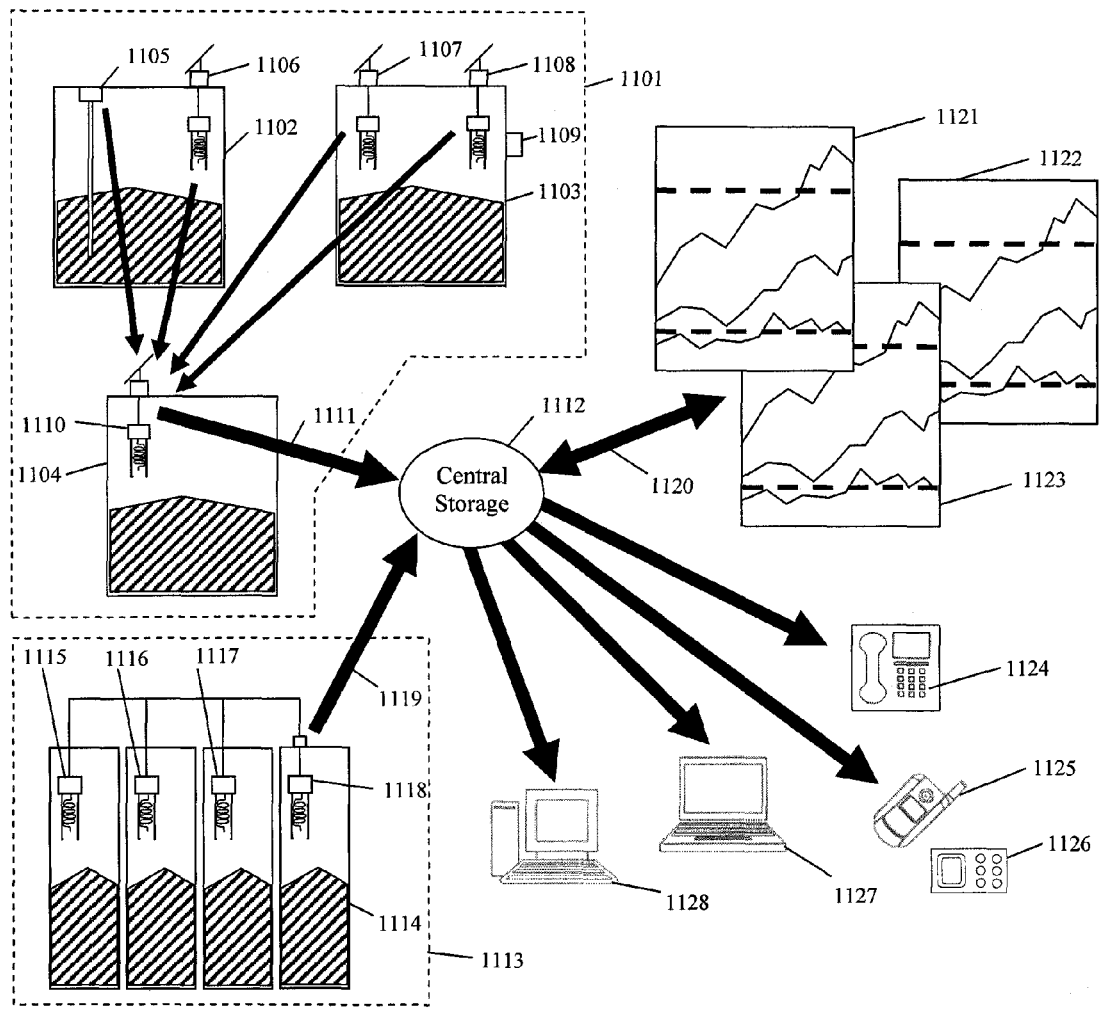
FIG. 11 is a diagrammatic illustration of an exemplary system of multiple site networks of grain spoilage detectors and other environmental detectors permanently installed in grain storage bins communicating data relating to $CO_2$ concentration, grain temperature, air temperature, relative humidity and outside weather conditions to a central data storage node where the data are processed for the presence of alert or alarm conditions and appropriate user messages are generated and transmitted.

FIG. 11 illustrates a generic example of a system of networks of $CO_2$ detectors and other detectors, both inside and outside grain storage bins. Each site network aggregates site data from a mesh of site detectors. In this illustration, the first networked site 1101 contains three monitored grain storage bins 1102, 1103 and 1104. Each bin contains a variety of sensors: a cabled temperature detector 1105 and a $CO_2$ detector 1106, a $CO_2$ detector 1107, an internal weather station 1108 and an external weather station 1109, and a $CO_2$ detector 1110. In this example, the $CO_2$ detector in the third bin 1110 acts as a data collection and transmission node for the site. The other detectors send their data via short range radio frequency techniques to the collection node detector which, in turn, forwards all of the $CO_2$ and other detector data 1111 for the site network of detectors to a central data storage system 1112 via long range radio frequency or cellular telephone techniques. This is replicated for any number of other different sites where local detector networks are established inside and outside grain storage bins. This is illustrated, for example, by a second networked site 1113. Here, the site contains four monitored bins 1114, each with a permanently installed $CO_2$ detector system 1115, 1116, 1117 and 1118. In this network, the fourth $CO_2$ detector 1118 acts as a data collection and transmission node for the site. The other detectors send their data via short range radio frequency techniques to the collection node detector which, in turn, forwards all of the detector data 1119 for the site network of detectors to a central data storage system 1112 via long range radio frequency or cellular telephone techniques. All data from the various networked sites is processed by the central data storage system and formatted for display 1121, 1122, and 1123 of $CO_2$ and other data over time for each monitored grain bin in the system with appropriate alarms and alerts noted. The $CO_2$ data and alert/alarm status are available for inspection by operators or managers either locally or remotely via an internet computer connection 1120 to the central data storage system. In addition to handling information requests by internet connection, the central data storage system, in this embodiment, pushes alert and alarm messages to users and subscribers via hardwired telephone 1124, wireless cellphone 1125 and other handheld devices 1126, mobile computers 1127 and other computers 1128. Each networked site can comprise any number of permanently installed detectors including, but not limited to, $CO_2$, air temperature, relative humidity and grain temperature, can be embedded in the same local communication network or mesh and communicate their data to the detector acting as the site network's collection node via short range radio frequency techniques. Aggregated data is forwarded by this collection node to a central data storage system via long range radio frequency or cellular telephone methods. Data communication among detectors in each site mesh or network can also be performed over wires or via any combination of wired and wireless data links.

With further reference to FIG. 11, a particular embodiment of the $CO_2$ detector assembly 1106 is comprised of:

- Hammond PJ-1086T control electronics enclosure,
- Custom universal control and power (UCAP) custom printed circuit board assembly with Freescale model MC9S08QE128 microprocessor and XBee-PRO XSC short range radio transceiver model XBP09-XC009-DK and half-wave antenna model A09-HASM-675
- All Electronics model SS1203A battery charge controller,
- HQRP-Amazon Model O-SOP-25A 6W solar panel,
- Power Sonic model PS-1270F1 12V/3A battery,
- CalAmp Landcell model SMC-GPRS-GEN cellular modem and model ANT-GSMQB-MMCX antenna,
- R.F. Solutions, Limited, model AN-GSMQB-MMCX cellular modem antenna,
- Hammond model 15OZGRP083 enclosure,
- custom master/slave sensor board (MSSB) printed circuit board assembly with Freescale model MC9S08GT16 microprocessor,
- GE-Telaire model 6615-5K $CO_2$ sensor engine,
- GE Sensors temperature and relative humidity sensor model Chipcap-D.
- 4 inch diameter PVC pipe for the dust shroud,
- 4 inch diameter PVC endcap,
- coiled 24 inch length of 0.375 inch inner diameter nylon recoil hose for the dust excluder and
- MSSB to UCAP interconnect cable, outdoor rated 4-pair CAT5.

The central data storage system 1112 of this embodiment is located on a Dell 1650 1U Server with a dual P3 1400 GHz processor, 1 GB SDRAM memory, a Perc/3 RAID controller and three 36 GB Ultra3 SCSI drives running in RAID 5 configuration with 72 GB usable storage. The server operating system is Ubuntu Server Edition V9.10 running Linux. Internet web pages are generated using Apache Tomcat and Ruby on Rails V2.3 software; the database is implemented with MySQL Enterprise software; user authentication is handled using the Remote Authentication Dial In User Service (RADIUS) protocol; the general purpose programming language is Regina Rexx V3.5.

Data is organized for viewing 1121, 1122 and 1123, using MySQL Enterprise and amCharts version 1.6.0.0. Data charts are delivered to user web browsers on web pages created using Apache Tomcat. Alarming and notification software programs are also resident on the central data storage system and are custom algorithms implemented using Regina Rexx V3.5. In addition to web page presentation, alarm and notification messages are formatted and sent to users via methods including, but not limited to, landline telephone 1124, cellular telephone 1125, custom handheld devices 1126, wireless computer 1127 and landline-connected computers 1128.

Figure 12:
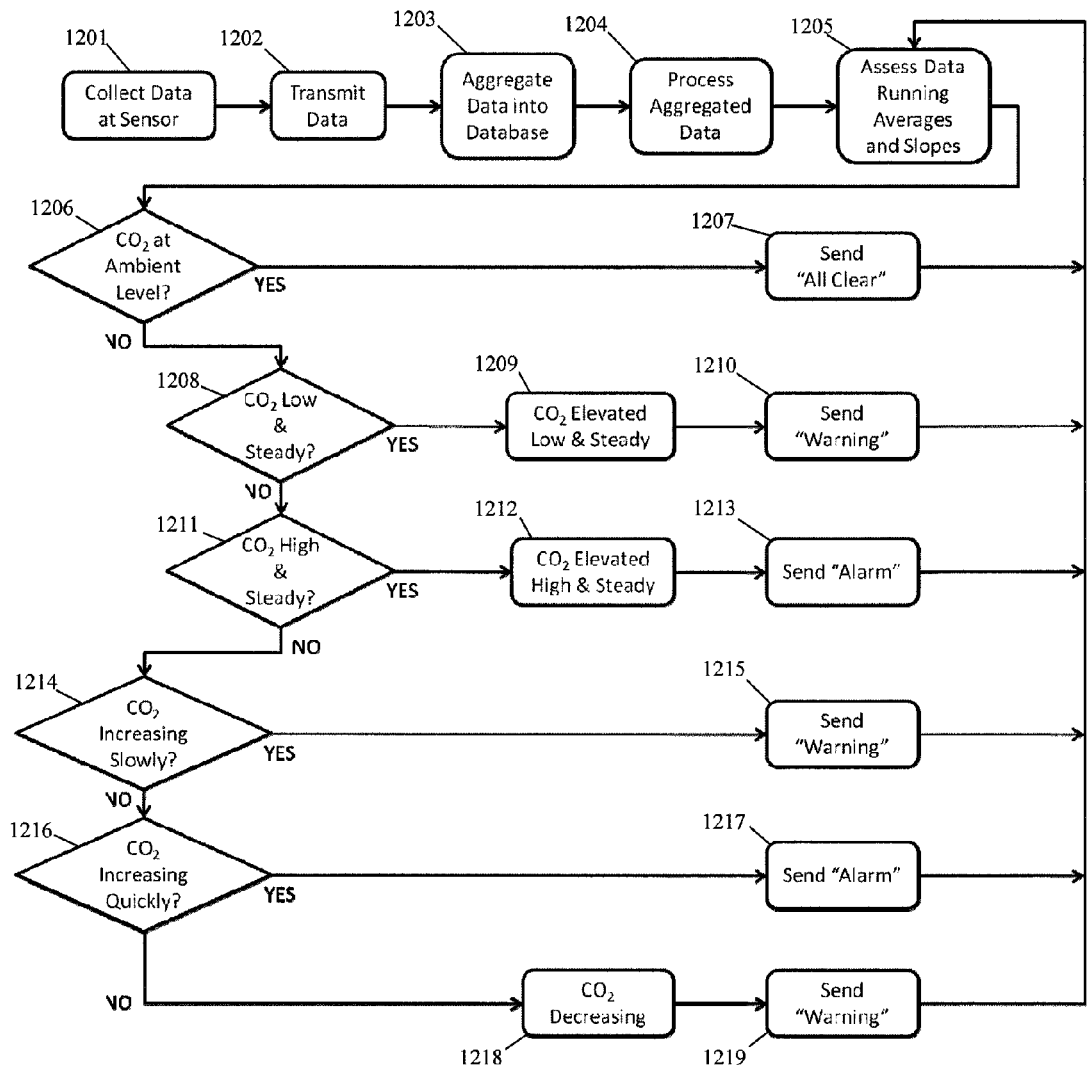
FIG. 12 is a diagrammatic flow chart of an exemplary data collection, processing, analysis, decision-making and alert messaging system illustrating how information is moved, manipulated and acted upon by elements of the present invention, including the detector sensor system and its telecommunication subsystem as well as the secure central data storage system.

FIG. 12 shows an exemplary system flowchart describing a process for data collection, analysis, decision-making and alert messaging related to $CO_2$ status and $CO_2$ trends within monitored grain bins. $CO_2$ and other data, which may include, but is not limited to, temperature and relative humidity, is collected 1201 by one or more sensors in monitored grain bins or grain ground piles. These data are transmitted to a secure central server 1202, such as via radio or cellular technology, although any suitable communications may be used. The data are aggregated into a database file 1203 where they are organized by sensor and storage site identifiers. The data are then processed 1204 to identify parameter levels, averages and trends as well as processed for viewing by users and analysts. The processed data are analyzed 1205 by trained people or by programmed computer systems to identify the status of the stored grain, on the basis of which a number of potential decisions and actions are possible. $CO_2$ is used as an example in this figure. The level of $CO_2$ is compared 1206 to normal ambient levels of this gas. If the level is at or near historical ambient levels, then an "all clear" message 1207 is issued to the database and to the user. If the level is above ambient, then a determination is made regarding the rate of change of the $CO_2$ level. If the elevated level is below an established threshold and constant or near constant 1208, then the level is determined to be elevated, low and steady 1209 and a "warning" message 1210 is issued to the database and to the user. If the elevated level is above an established threshold and constant or near constant 1211, then the level is determined to be elevated, high and steady 1212 and a "warning" message 1213 is issued to the database and to the user. If the elevated level is changing, then a determination is made regarding the rate of change. A slow rate of change 1214 results in the issuance of a "warning" message 1215 to the database and to the user. If the rate of change is above a predetermined threshold rate 1216, then an "alarm" message 1217 is issued to the database and to the user. If the $CO_2$ level is changing, but not increasing, then it is decreasing 1218 and a "warning" message 1219 is issued to the database and to the user. As data are accumulated over time, the assessment of data and traversal of this decision tree are periodically repeated based on the needs of the system users.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for measuring and reporting spoilage gas concentration in an airspace over stored grain within grain storage bins comprising:
   a) a filterless passive dust exclusion device comprising an enclosed pathway with an inlet adapted to be exposed to air of the bulk grain storage bin, an outlet adapted to be connected to a gas detector for measuring spoilage gas concentration, and a non-linear path between said inlet and outlet, wherein a velocity of air present at said inlet is substantially reduced prior to reaching said outlet such that the amount of dust in the sampled air is substantially reduced, and the spoilage gases are delivered to the gas detector by diffusion;
   b) said gas detector connected to said dust exclusion device;
   c) a control processor that directs gas detector operation and collection of gas concentration data;
   d) a transmitter communicably connected to said control processor that transmits collected gas concentration data to a receiver;
   e) a display connected to said receiver configured to display the collected gas concentration data as measured over time.

2. The apparatus according to claim 1, wherein said apparatus further comprises a solar energy collection and conversion panel.

3. The apparatus according to claim 2, wherein said apparatus further comprises a battery interconnected to provide operating power to said gas detector and electrically interconnected to said solar energy collection and conversion panel.

4. The apparatus according to claim 3, wherein said apparatus further comprises battery charging control circuitry interconnected between said solar energy collection and conversion panel and said battery.

5. The apparatus according to claim 1, wherein said apparatus further comprises a system to provide alert and alarm messages appropriate to the detected spoilage gas level.

6. The apparatus according to claim 1, wherein said apparatus further comprises a system capable of assessing the level and type of biological activity responsible for generating the detected spoilage gas.

7. The apparatus according to claim 1, wherein said spoilage gas is carbon dioxide and said gas detector is a carbon dioxide detector and said gas concentration is carbon dioxide concentration.

8. An apparatus for use in detection of spoilage gases in a bulk grain storage bin that substantially reduces the amount of dust in sampled air comprising:
   an enclosed pathway comprising (a) an inlet adapted to be exposed to air of the bulk grain storage bin, (b) an outlet adapted to be connected to a gas sensor for said detection of spoilage gases, and (c) a non-linear path between said inlet and outlet, wherein a velocity of air present at said inlet is substantially reduced prior to reaching said outlet such that the amount of dust in the sampled air is substantially reduced, and the spoilage gases are delivered to the gas detector by diffusion.

9. The apparatus according to claim 8 wherein said non-linear path is a serpentine path within a machined, formed or injection molded component.

10. The apparatus according to claim 8, wherein said enclosed pathway comprises a housing containing at least first and second baffles arranged within said housing to form said non-linear path.

11. The apparatus according to claim 8, wherein said non-linear path is configured to change the direction of air flow at least 90 degrees at least three times between said inlet and outlet.

12. The apparatus according to claim 8, wherein said enclosed pathway further comprises a tubular member, said inlet being a first end of said tubular member, said outlet being a second end of said tubular member, and said non-linear path being a non-linear configuration of a portion of said tubular member intermediate of said first end and said second end.

13. The apparatus according to claim 12, wherein said tubular member has a coiled configuration.

14. The apparatus according to claim 12, wherein said tubular member has a serpentine configuration.

15. An apparatus for use in detection of spoilage gases in a bulk grain storage bin that substantially reduces the amount of dust in sampled air comprising:
   a tubular member comprising an inlet at a first end thereof and an outlet at a second end thereof, said second end adapted to be connected to a gas detector for said detection of spoilage gases, and said first end adapted to be exposed to air of the bulk grain storage bin, said tubular member comprising a non-linear pathway between said first and second ends and a velocity of air present at said first end is substantially reduced prior to reaching said second end; wherein the amount of dust in the sampled air is substantially reduced, and the spoilage gases are delivered to the gas detector by diffusion.

16. The apparatus according to claim 1 wherein said tubular member comprises a coiled tube.

* * * * *